United States Patent
Lai et al.

(10) Patent No.: US 7,377,777 B2
(45) Date of Patent: May 27, 2008

(54) ORTHODONTIC APPLIANCE WITH ARCHWIRE-ENGAGING CLIP

(75) Inventors: Ming-Lai Lai, Arcadia, CA (US); Ajay Myer, Irvine, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/317,274

(22) Filed: Dec. 23, 2005

(65) Prior Publication Data

US 2007/0148610 A1    Jun. 28, 2007

(51) Int. Cl.
*A61C 3/00* (2006.01)
(52) U.S. Cl. .................. 433/11; 433/8; 433/10
(58) Field of Classification Search .................. 433/11, 433/8, 10
See application file for complete search history.

(56) References Cited

U.S. PATENT DOCUMENTS

| | | |
|---|---|---|
| 1,991,047 A | 2/1935 | Boyd et al. |
| 3,327,393 A | 6/1967 | Brader |
| 3,724,074 A | 4/1973 | Wallshein |
| 4,103,423 A | 8/1978 | Kessel |
| 4,171,568 A | 10/1979 | Forster |
| 4,527,975 A | 7/1985 | Ghafari et al. |
| 4,551,094 A | 11/1985 | Kesling |
| 4,712,999 A | 12/1987 | Rosenberg |
| 5,269,681 A | 12/1993 | Degnan |
| 5,358,402 A | 10/1994 | Reed et al. |
| 5,366,372 A | 11/1994 | Hansen et al. |
| 5,380,196 A | 1/1995 | Kelly et al. |
| 5,439,379 A | 8/1995 | Hansen |
| 5,474,445 A | 12/1995 | Voudouris |
| 5,516,284 A | 5/1996 | Wildman |
| 5,630,715 A | 5/1997 | Voudouris |
| 5,685,711 A | 11/1997 | Hanson |
| 5,711,666 A | 1/1998 | Hanson |
| 5,857,850 A | 1/1999 | Vourdouris |
| 5,863,199 A | 1/1999 | Wildman |
| 6,302,688 B1 | 10/2001 | Jordan et al. |
| 6,325,622 B1 | 12/2001 | Kelly et al. |
| 6,582,226 B2 | 6/2003 | Jordan et al. |
| 6,648,638 B2 | 11/2003 | Castro et al. |
| 6,957,957 B2 * | 10/2005 | Pospisil ................... 433/11 |
| 2004/0086825 A1 | 5/2004 | Lai et al. |
| 2004/0086826 A1 | 5/2004 | Pospisil |
| 2005/0095549 A1 | 5/2005 | Cinader et al. |
| 2005/0123875 A1 | 6/2005 | Stadtmiller et al. |
| 2005/0170308 A1 | 8/2005 | Lai et al. |
| 2006/0024635 A1 | 2/2006 | Lai |
| 2006/0147868 A1 | 7/2006 | Lai et al. |

FOREIGN PATENT DOCUMENTS

WO    WO 98/20805    5/1998

* cited by examiner

*Primary Examiner*—Cris Rodriguez
*Assistant Examiner*—Candice C Stokes
(74) *Attorney, Agent, or Firm*—James D. Christoff

(57) ABSTRACT

An orthodontic appliance includes a latch that comprises at least one clip for retaining an archwire in an archwire slot of the appliance. The clip includes a first section, a second section opposed to the first section and a third section that interconnects the first section and the second section. The third section is adjacent the base and includes an outer edge having a convex shape in contact with a wall portion of the base. The convex shape facilitates opening the clip during insertion of an archwire into the archwire slot of the appliance.

23 Claims, 4 Drawing Sheets

ORTHODONTIC APPLIANCE WITH ARCHWIRE-ENGAGING CLIP

BACKGROUND OF THE INVENTION

1. Field of the Invention

This invention broadly relates to appliances that are used to move teeth during the course of orthodontic treatment. More particularly, the present invention relates to a self-ligating orthodontic appliance such as a bracket or molar appliance having a latch with at least one clip that releasably retains an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment typically enhances the aesthetic appearance of the teeth, particularly in instances when the patient's front teeth are malpositioned or crooked. Orthodontic treatment can also improve the patient's occlusion so that the teeth function better with each other during mastication.

Many types of orthodontic treatment programs involve the use of a set of tiny appliances and wires that are commonly known collectively as "braces". During such treatment programs, small slotted appliances known as brackets are fixed to the patient's anterior, cuspid and bicuspid teeth, and an archwire is inserted into the slot of each bracket. The archwire forms a track to guide movement of the teeth to orthodontically correct locations. End sections of the archwires are typically captured in molar appliances that are fixed to the patient's molar teeth.

Recently, there has been increased interest in orthodontic appliances that have a latch for retaining the archwire in the archwire slot. Appliances of this type are widely known as self-ligating appliances and often obviate the need to use ligatures (such as wire ties or elastomeric O-rings) for retaining the archwire in the archwire slots. Improved self-ligating orthodontic appliances having a self-releasing latch are described in applicant's U.S. Pat. Nos. 6,302,688 and 6,582,226.

A recently introduced self-ligating appliance known as "SMARTCLIP" brand appliance from 3M Unitek Corporation has a latch that comprises two resilient clips, and each clip has a generally "C"-shaped configuration. The clips spread open to admit an archwire into an archwire slot of the appliance. Each clip is connected to a body of the appliance by a post that extends through the clip, and an outwardly extending base of the appliance helps to retain the clip in place on the post.

SUMMARY OF THE INVENTION

The present invention is directed toward an orthodontic appliance having an archwire-engaging latch that includes at least one clip. Each clip includes three sections, one of which has an outer edge that is in contact with a wall portion of a base of the appliance. The outer edge has a convex shape that facilitates opening of the clip during engagement with an archwire. As a result, less force is needed to insert the wire into the clip during the course of orthodontic treatment.

In more detail, the present invention in one aspect is directed to an orthodontic appliance that comprises a base, a body extending outwardly from the base, and an archwire slot extending across the appliance in a generally mesial-distal direction. The appliance also includes a post extending outwardly from the body, and a latch for releasably retaining an archwire in the archwire slot. The latch comprises a clip with a first section, a second section opposed to the first section and a third section interconnecting the first section and the second section. The clip also includes a region between the first section and the second section for receiving an archwire when an archwire is placed in the archwire slot. The third section has an outer edge facing away from the archwire-receiving region, and the base includes a wall portion in contact with the outer edge. The outer edge of the third section that is in contact with the wall portion has a convex shape.

Another aspect of the invention is also directed to an orthodontic appliance that comprises a base, a body extending outwardly from the base, and an archwire slot extending across the appliance in a generally mesial-distal direction. The appliance also includes a latch for releasably retaining an archwire in the archwire slot. The latch comprises a clip with a first section, a second section opposed to the first section and a third section interconnecting the first section and the second section. The clip also includes a region between the first section and the second section for receiving an archwire when an archwire is placed in the archwire slot. The third section has an outer edge facing away from the archwire-receiving region. The appliance also includes structure for coupling the clip to the body and a wall portion in contact with the outer edge. The outer edge of the third section that is in contact with the wall portion has a convex shape.

When the clip is opened to receive an archwire, the first section and the second section move away from each other. At the same time, the third section flexes in areas next to the base. The convex shape of the outer edge of the third section facilitates bending movement of the third section as the clip opens, and helps to ensure that only a relatively small portion of the outer edge is in contact with the base.

The construction of the clip of the present invention is an advantage during engagement of an archwire with the appliance. As the archwire is pushed into the archwire slot of the appliance and enters the archwire-receiving region of the clip, the force needed to open the clip is reduced. As a consequence, the probability that the patient will experience discomfort during archwire engagement is also reduced. This aspect is particularly important for patients having teeth that are relatively sensitive to pain or are relatively mobile in the dental arch.

Additional aspects and features of the invention are set out in the detailed description that follows and are illustrated in the accompanying drawings.

DEFINITIONS

Figure 1:
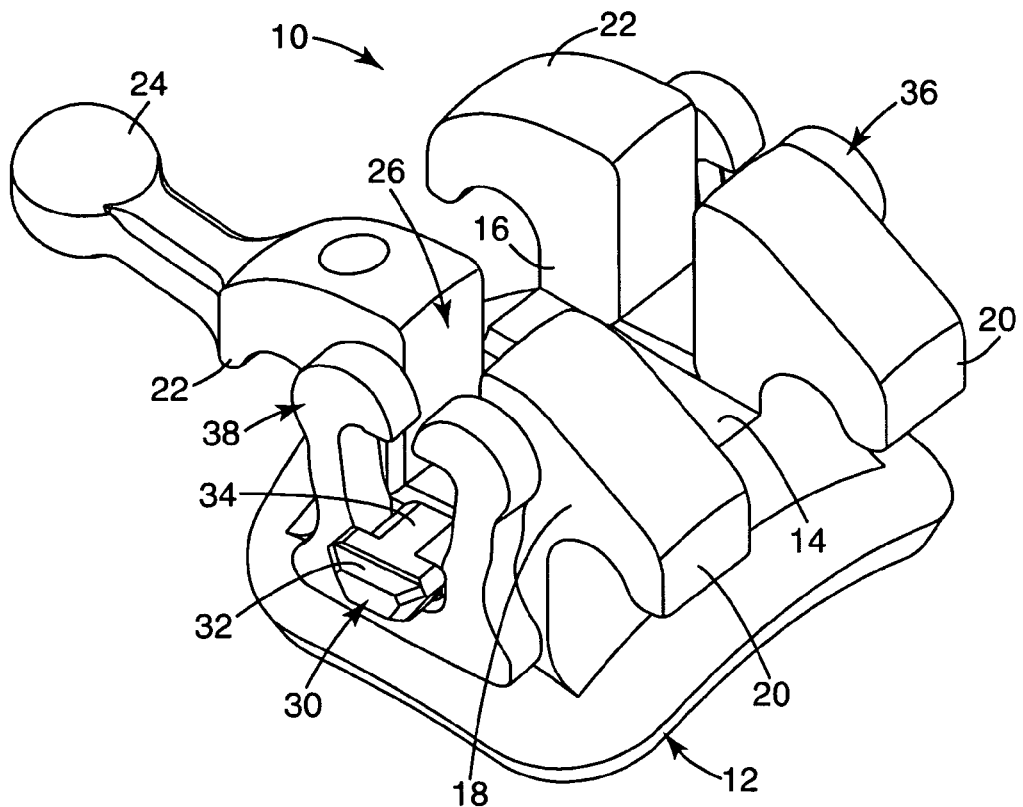
FIG. 1 is a perspective view of an orthodontic appliance constructed in accordance with one embodiment of the present invention, looking at the appliance toward its distal, facial and occlusal sides.
Figure 2:
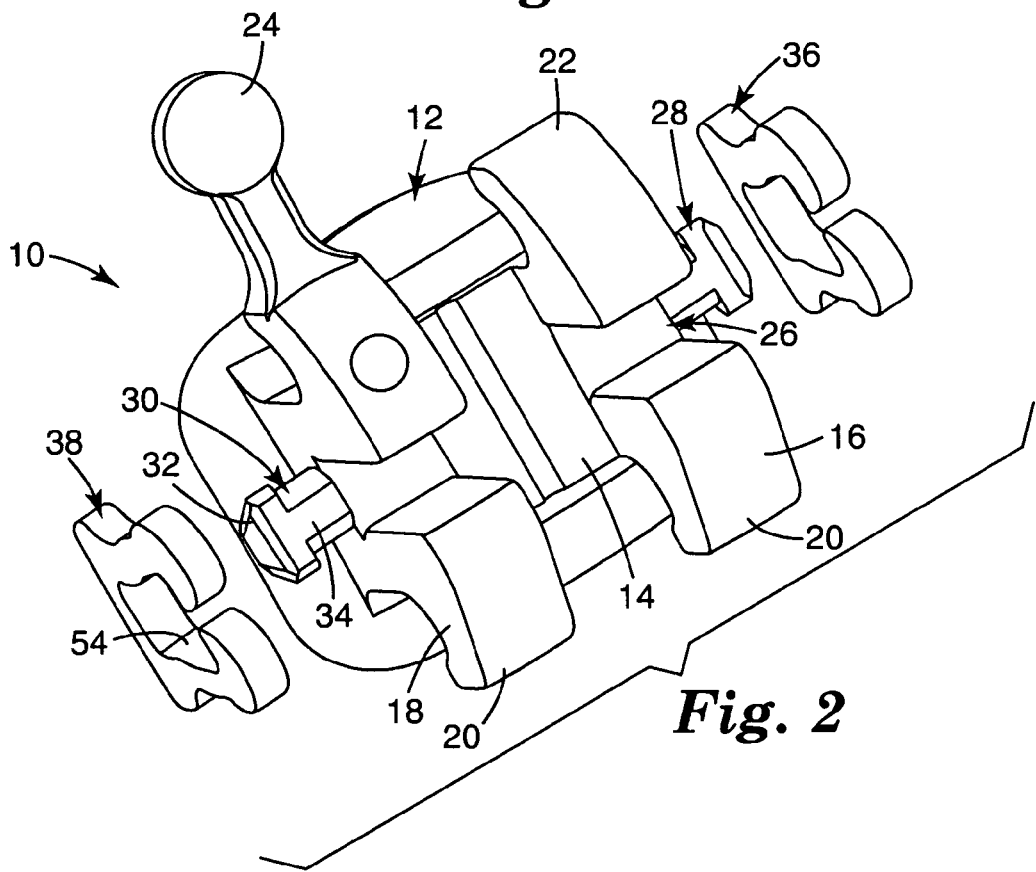
FIG. 2 is an exploded perspective view of the appliance depicted in FIG. 1, looking at the appliance toward its distal, facial and occlusal sides in a somewhat different direction compared to FIG. 1.
Figure 3:
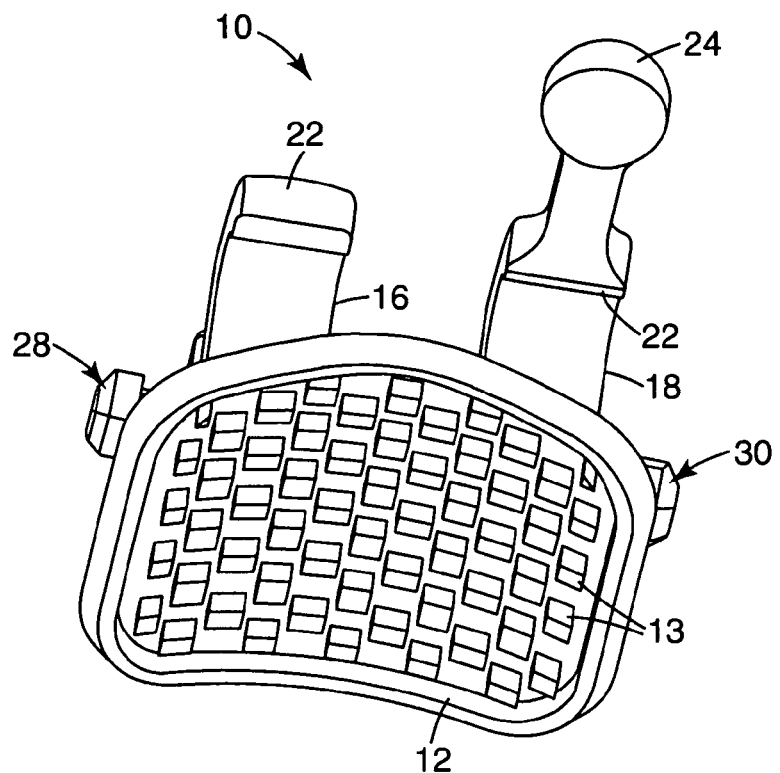
FIG. 3 is a rear view of the appliance shown in FIGS. 1 and 2, looking in a direction toward its lingual and gingival sides.
Figure 4:
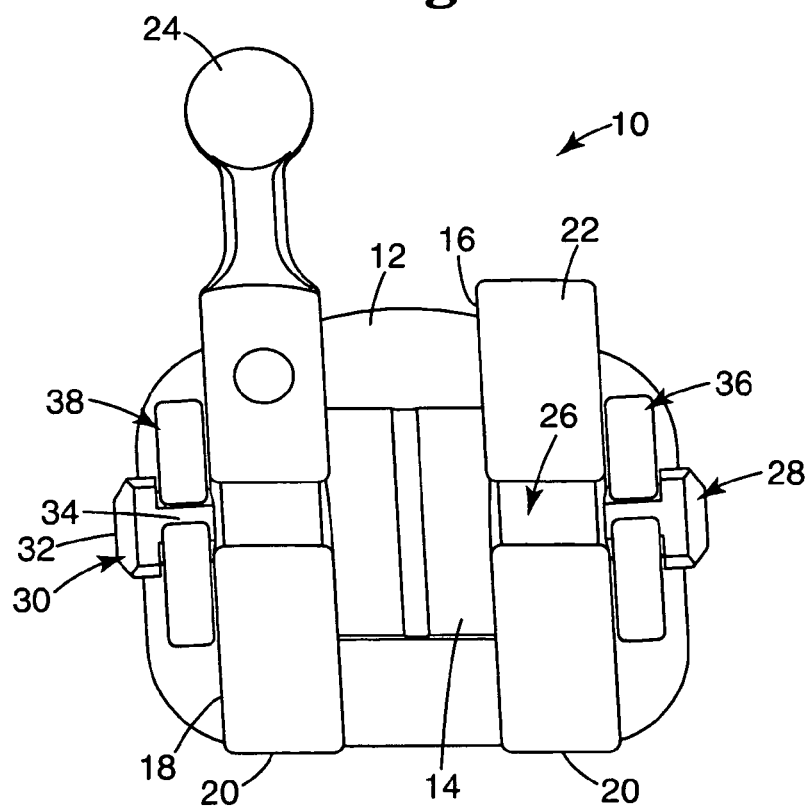
FIG. 4 is an assembled, front elevational view of the appliance shown in FIGS. 1-3, looking at the appliance toward its facial side.
Figure 5:
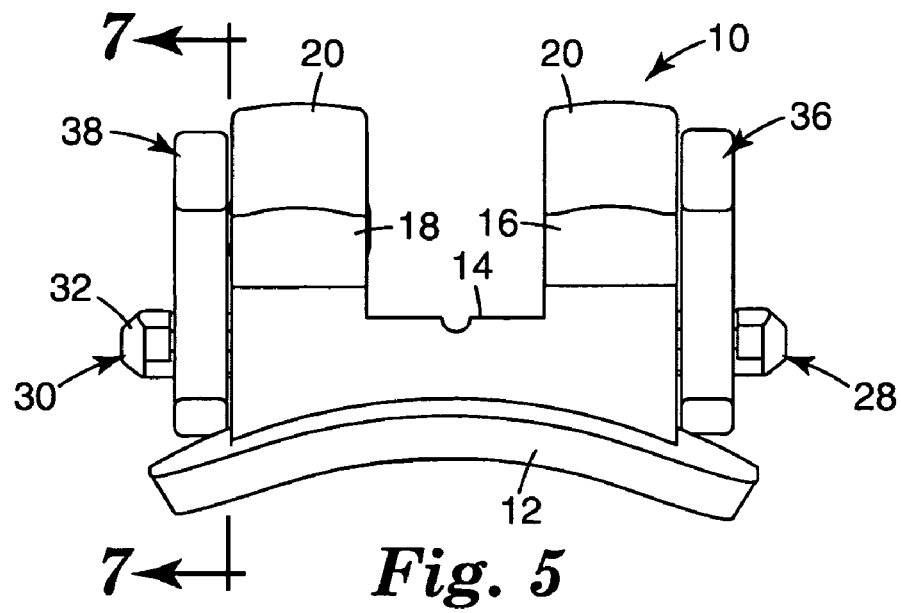
FIG. 5 is a side elevational view of the appliance illustrated in FIGS. 1-4, looking at the appliance toward its occlusal side.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

An orthodontic appliance constructed in accordance with one embodiment of the present invention is illustrated in FIGS. 1-6 and is broadly designated by the numeral 10. The appliance 10 in this instance is an orthodontic bracket that is adapted to be secured to an enamel surface of a patient's tooth, such as a facial tooth surface. Alternatively, the appliance could be a molar appliance, an appliance for attachment to a lingual tooth surface, or any other appliance that is adapted to receive an archwire for controlling movement of the associated tooth during the course of orthodontic therapy.

The appliance 10 includes a base 12 for bonding the appliance 10 directly to the patient's tooth enamel by the use of an adhesive. Preferably, the base 12 has an outwardly facing concave compound contour that matches the convex compound contour of the patient's tooth surface to which it is bonded. Optionally, the base 12 is provided with grooves, projections, particles, recesses, undercuts, a chemical bond enhancement material or any other material or structure, or any combination of the foregoing that facilitates bonding of the appliance 10 directly to the patient's tooth surface. In the illustrated embodiment, the base 12 includes a series of spaced-apart projections 13 that each extend in a generally lingual direction.

A body 14 extends outwardly from the base 12 in a generally facial direction. The body 14 includes a mesial body portion 16 and a distal body portion 18 that is spaced from the mesial body portion 16. In this embodiment, each of the portions 16, 18 includes an occlusal tiewing 20 and a gingival tiewing 22, although one or more of the tiewings 20, 22 could be omitted if desired. In addition, one of the gingival tiewings 22 is integrally connected to a ball hook 24.

Preferably, and as shown in the drawings, the body 14 (including the body portions 16, 18 and the hook 24) is integrally connected to the base 12, and the body 14 and the base 12 form a single, unitary component. This unitary component may be made, for example, in a machining or molding process such as metal injection molding. However, other constructions are also possible. For example, the base and the body could be separately manufactured and then later assembled together using a joining operation such as a welding or brazing process.

The appliance also includes an archwire slot 26 that longitudinally extends in a generally mesial-distal direction across the appliance 10, including through a channel of the body portions 16, 18. Each of the tiewings 20, 22 extends over a recess or notch for receiving a ligature (not shown) for assistance in retaining an archwire in the archwire slot 26. However, the provision of the tiewings 20, 22 and the use of a ligature are optional and may only be needed in certain instances, such as in instances where the tooth is severely malpositioned during the initial stages of treatment.

The appliance 10 includes a mesial post 28 and a distal post 30 that are integrally connected to the mesial body portion 16 and the distal body portion 18 respectively. The posts 28, 30 extend outwardly in opposite directions away from each other and from the body 14. Preferably, each post 28, 30 extends along a reference axis that is parallel to the longitudinal axis of the archwire slot 26. As shown for example in FIGS. 5 and 6, the posts 28, 30 are located in a lingual direction relative to the archwire slot 26.

The distal post 30 includes an outermost head 32 and a neck 34 that integrally interconnects the head 32 and the distal body portion 18. The neck 34 has a generally rectangular cross-sectional configuration when considered in reference planes perpendicular to the reference axis along which the post 30 extends or when considered in reference planes generally perpendicular to a mesial-distal axis. Preferably, the occlusal, gingival and lingual sides of the neck 34 in regions along the innermost or distal end of the neck 34 include curved or chamfered sections that are connected to the distal side of the distal body portion 18, for enhancing the strength of the connection between the distal post 30 and the body 14.

Figure 6:
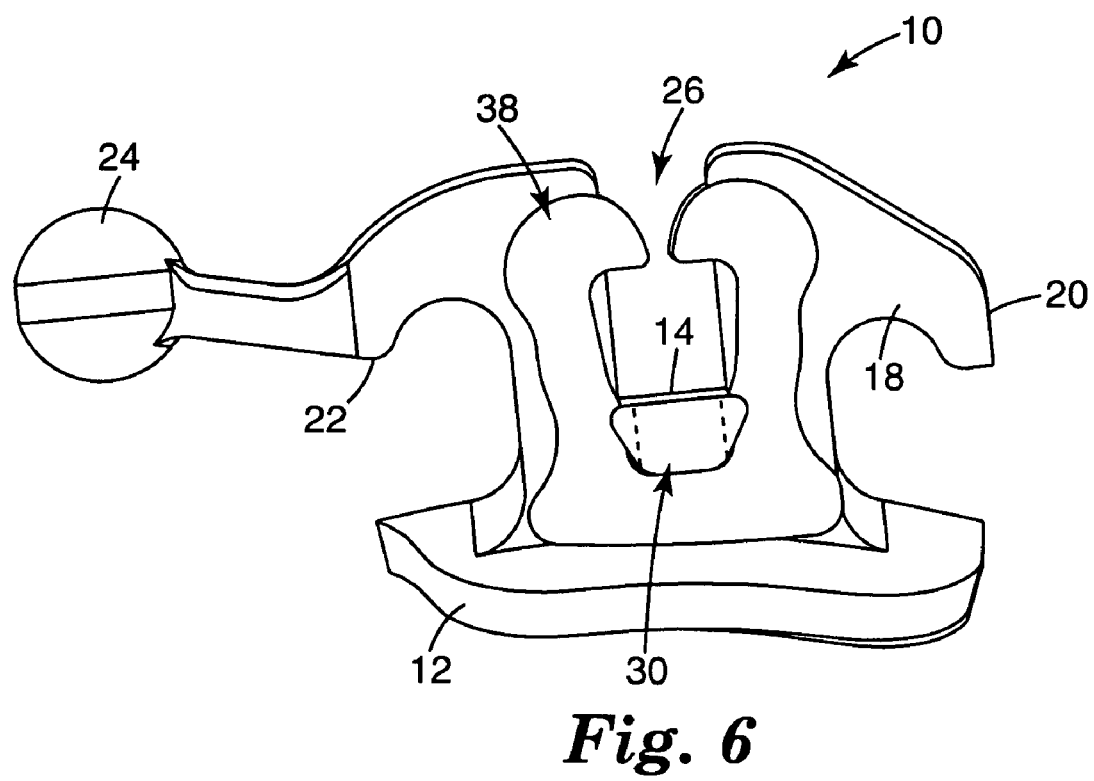
FIG. 6 is a side elevational view of the appliance shown in FIGS. 1-5, looking at the appliance toward its distal side.

As shown for example in FIG. 6, the head 32 of the post 30 has a generally trapezoidal configuration when viewed in a mesial direction, or when viewed in reference planes that are perpendicular to the reference axis along which the post 30 extends. FIG. 6 also illustrates in dashed lines the cross-sectional shape of the neck 34 for purposes of comparison. As illustrated, the height of the neck 34 and the height of the head 32 are essentially the same along the lingual side of the post 30 when considered in directions along an occlusal-gingival reference axis. However, along the facial side of the post 30, the height of the head 32 is greater than the height of the neck 34 when considered in directions along an occlusal-gingival reference axis.

The head 32 extends outwardly past the neck 34 a certain distance when considered in reference planes perpendicular to a mesial-distal reference axis or when considered in reference planes perpendicular to the reference axis along which the post 30 extends. In the illustrated embodiment, the head 32 extends outwardly past the neck 34 in at least one, and preferably in both directions along an occlusal-gingival reference axis. In the illustrated embodiment, this certain distance is determined by adding the distance that the head 32 extends past the neck 34 in an occlusal direction to the distance that the head 32 extends past the neck 34 in a gingival direction. This certain distance decreases as the lingual side of the post 30 is approached and as a third section 46 of the clip 38 (as described below) is approached. This relationship is shown by the dashed lines in FIG. 6 illustrating the occlusal and gingival sides of the neck 34, in comparison to the full lines that depict the occlusal and gingival sides of the head 32. Preferably, this certain distance is zero or approximately zero in regions adjacent the third section 46.

Additional information regarding the post 30 is described in applicant's published U.S. patent application no. 2006/0024635-A1.

The appliance 10 also includes a latch for releasably retaining an archwire in the archwire slot 26. In the illustrated embodiment, the latch includes a mesial clip 36 that is connected to the mesial post 28, and a distal clip 38 that is connected to the distal post 30.

Figure 7:
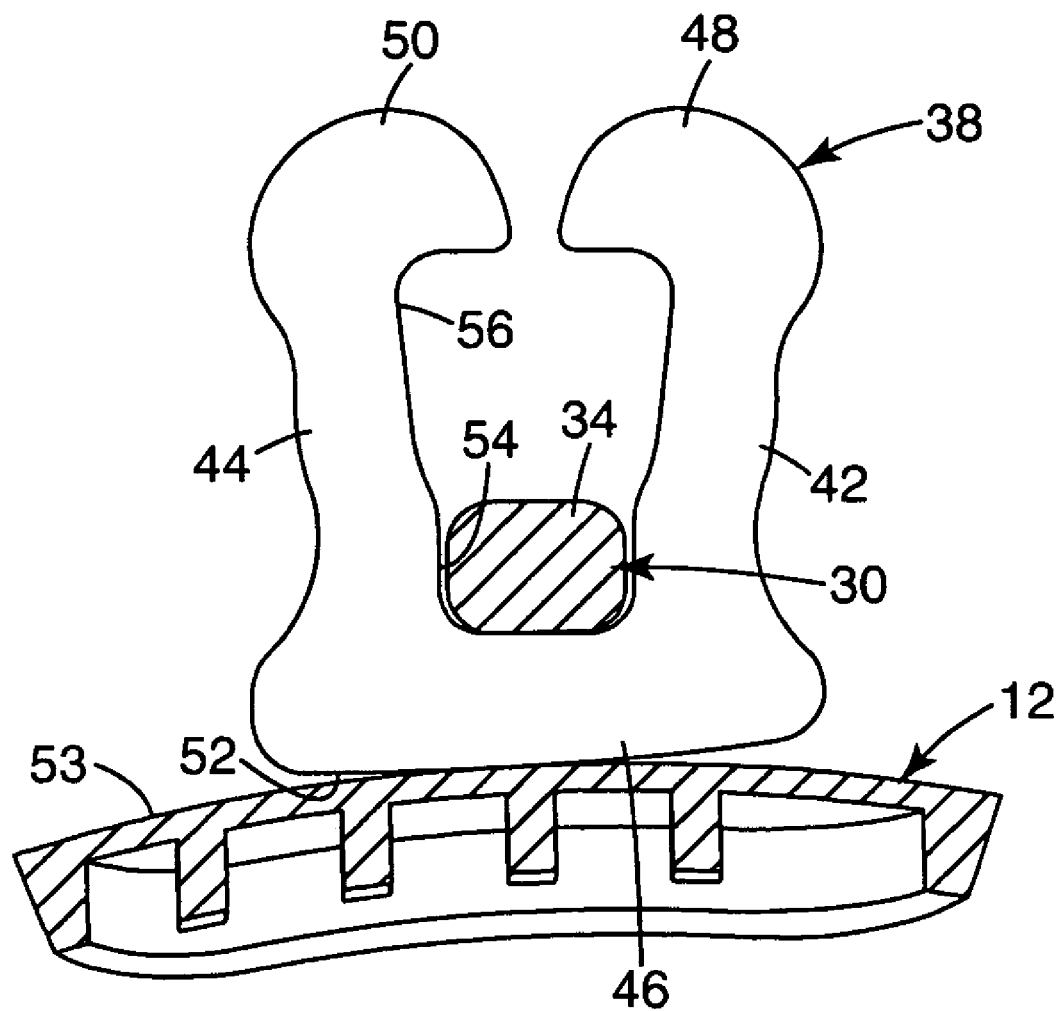
FIG. 7 is an enlarged side elevational view in partial cross-section depicting a portion of the appliance of FIGS. 1-6 including a distal clip and a portion of the appliance base, taken along lines 7-7 of FIG. 5.

The distal clip 38 and the neck 34 are shown alone in FIG. 7. The distal clip 38 includes an elongated occlusal or first section 42, an elongated second or gingival section 44 and an elongated lingual or third section 46. The first and second sections 42, 44 extend in generally parallel directions that lie along a generally facial-lingual reference axis when the clip 36 is relaxed and the third section 46 extends in a generally occlusal-gingival direction. In instances where the appliance has zero torque angle, such as the appliance 10 shown in the drawings, the third section 46 is generally perpendicular to the direction of extension of the sections 42, 44.

The third section 46 also integrally connects the first and second sections 42, 44. An outer, lingual edge 52 of the third section 46 faces the base 12 and preferably has a smoothly curved shape along its entire extent. As illustrated in FIG. 7, a portion of the outer edge 52 near the middle of the third section 46 is in contact with a wall portion 53 of a facial side of the base 12, and at least this portion of the outer edge 52 has a convex shape.

Outer ends of the sections 42, 44 are integrally connected to arm portions 48, 50 respectively. A facial edge of each arm portion 42, 44 is smoothly curved in an arc about a mesial-distal reference axis.

The sections 42, 44, 46 extend along the occlusal, gingival and lingual sides of the neck 34 respectively. A rear or lingual portion of the first and second sections 42, 44, along with the third section 46 together at least partially define a recess 54 (see, e.g., FIG. 2) for receiving the neck 34 of the post 30.

A front (facial) portion of the first and second sections 42, 44, along with the arm portions 48, 50 and a portion of the facial side of the neck 34, together at least partially define a region 56 (FIG. 7) for receiving an archwire. As shown for example in FIG. 5, the region 56 is aligned with the archwire slot 26. Overall, the clip 38 presents a generally "C"-shaped configuration when looking in a mesial or distal direction.

The clip 38 is shown in its normal, relaxed orientation in the drawings. However, the arm portions 48, 50 are movable away from each other in order to admit the archwire 40 into the archwire-receiving region 56 when desired. As the arm portions 48, 50 move away from each other, the first and second sections 42, 44 deflect outwardly and bend in respective arcs away from each other.

The smooth, outer edge of the arm portions 48, 50 enables the clip 38 to open and admit the archwire into the region 56 by pressing the archwire against the outer curved edges of the arm portions 48, 50. As pressure is exerted by the archwire on the curved edges, the first and second sections 42, 44 deflect away from each other in order to admit the archwire into the region 56. As the sections 42, 44 move away from each other, the third section 46 also bends such that the outer curved edge 52 moves toward a straight configuration.

Once the archwire is received in the region 56, the inherent resiliency of the clip 38, and particularly the resiliency of the sections 42, 44, 46 enables the arm portions 48, 50 to spring back toward each other and toward their normal, relaxed configuration as shown in FIGS. 1-7 in order to retain the archwire in the archwire slot 26. Preferably, but not necessarily, the region 56 is somewhat larger than the cross-section of the archwire in directions along both an occlusal-gingival reference axis as well as along a facial-lingual reference axis, in order to avoid firm contact between the clip 38 and the archwire. The clip 38 (including the sections 42, 44, 46) is sufficiently stiff to retain the archwire in the archwire slot 26 during the course of treatment so long as the forces exerted by the archwire on the appliance 10 are below a certain minimum value in a generally facial direction (more particularly, in a direction opposite to the direction of insertion of the archwire into the archwire slot 26). However, whenever the forces exerted by the archwire on the appliance 10 in the same direction are greater than the minimum value, as might occur when unexpectedly high forces are encountered, the first and second sections 42, 44 deflect outwardly and the arm portions 48, 50 move apart from each other to open the clip 38 and release the archwire from the archwire slot 26. Further details regarding such forces are described in the aforementioned U.S. Pat. Nos. 6,302,688 and 6,582,226.

Optionally, and as shown in the embodiment of the appliance 10 set out in the drawings, the clip 36 is substantially identical to the clip 38 and the post 28 is substantially identical in mirror image to the post 30. The latch, comprising the clips 36, 38, preferably releases the archwire from the archwire slot 26 in a generally facial direction whenever the archwire exerts a force in the same direction on the appliance 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 26 during the normal course of orthodontic treatment. As such, the archwire can exert forces on the appliance 10 sufficient to carry out the treatment program and move the associated teeth as desired.

Preferably, the minimum value for self-release (i.e., self-opening) of the latch is substantially less than the force required in the same direction to debond the appliance 10 from the associated tooth. The minimum value for self-release of the latch is preferably less than about one-half of the force required in the same direction to debond the appliance 10 from the associated tooth. For example, if the expected bond strength of the adhesive bond between the appliance 10 and the associated tooth is 16 lbs (7.2 kg) in a facial direction, the latch is constructed to self-release the archwire whenever the archwire exerts a force in the same facial direction on the appliance 10 that is somewhat greater than about 8 lbs (3.6 kg).

To determine the force to release the latch, a section of archwire is selected having an area in longitudinally transverse sections that is complemental to (i.e., substantially fills) the cross-sectional area of the archwire slot 26. Next, a sling is constructed and is connected to the archwire section at locations closely adjacent, but not in contact with the heads of the posts 28, 30 including the head 32. Optionally, the sling is welded or brazed to the archwire section. Next, the sling is pulled away from the appliance 10 while the appliance 10 is held in a stationary position, taking care to ensure that the longitudinal axis of the archwire section does not tip relative to the longitudinal axis of the archwire slot 26. The force to release the latch may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y. to measure the force.

Preferably, the distance between the opposed ends of the arm portions 48, 50 is less than the overall occlusal-gingival dimension of the smallest archwire expected to be used during the course of treatment. The archwire need not fill the archwire slot 26 and flatly engage the wall portions defining the archwire slot 26 in all instances. For example, a somewhat smaller wire, and perhaps an archwire having a circular cross-sectional shape, may be used during a portion of the treatment program. The distance between the opposed ends of the arm portions 48, 50 is preferably selected so that a variety of archwires of different cross-sectional configurations may be used in connection with the appliance 10.

Preferably, and as mentioned above, the distal clip 38 is substantially identical to the mesial clip 36. Optionally, however, it is possible to construct the clips 36, 38 somewhat differently to address certain circumstances. For example, if a malpositioned tooth is initially oriented such that its mesial side is rotated in a lingual direction, it may be desirable to increase the stiffness of the mesial clip 36 so that a somewhat greater force is needed to release the archwire from the archwire slot 26 in comparison to the force needed to release the archwire from the distal clip 38. Other options are also possible.

Optionally, the spring clips 36, 38 are cut from a flat section of metallic stock material. Suitable metallic materials include shape memory alloys such as alloys of nitinol and beta-titanium. The clips 36, 38 may be cut from the stock material using a stamping, die cutting, chemical etching, EDM (electrical discharge machining), laser cutting or water jet cutting process. As another option, the clips 36, 38 could be formed and then heat-treated to set their shapes.

As presently preferred, the clips 36, 38 are made from flat annealed superelastic material (such as nitinol) having a pickled surface. Preferred nitinol materials have a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 36, 38 are first cut in a rough cutting EDM process, then cut along their edges for an additional one or more times using an EDM process in order to smooth the edges. Alternatively, a laser cutting process or chemical etching process could be used to make the clips 36, 38.

Optionally, the clips 36, 38 are constructed so that the longitudinal direction of the clip material, or the principal direction of grain flow of the clip material, is substantially parallel to the direction of extension of the first and second sections 42, 44 (i.e. a generally facial direction in the illustrated embodiment ). However, in instances where the clips 36, 38 are constructed with third sections 46 that are less resistant to bending, the principal direction of grain flow of the clip material is substantially parallel to the direction of extension of the third sections 46. As yet another alternative, the principal direction of grain flow may extend at an angle of approximately 45 degrees relative to the direction of extension of the third sections 46.

Subsequent to the EDM, laser cutting or chemical etching process, the clips 36, 38 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8 (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Other optional aspects of the clips 36, 38 are described in applicant's published U.S. Patent Application entitled "ORTHODONTIC APPLIANCE WITH FATIGUE-RESISTANT ARCHWIRE RETAINING LATCH"; No. 2004/0086825, published May 18, 2004.

To assemble the appliance 10, the clip 38 is opened by moving the sections 42, 44 in directions away from each other a distance sufficient to clear the head 32 and enable the neck 34 to be received in the recess 34 by moving the clip 38 in a distal direction. Next, pressure on the sections 42, 44 is relieved and the clip 38 springs back to its normal, relaxed configuration such as shown in FIGS. 1 and 4-6 whereupon it is held in place by the head 32. The clip 36 is installed in a similar manner.

As an alternative to the appliance 10 shown in the drawings, the appliance may be constructed with a latch having one or more clips that are coupled to the body of the appliance in another manner. For example, the appliance may have a central cavity between the tiewings, and a clip that is retained in the cavity for retaining an archwire in an archwire slot of the appliance. The clip may be retained in the cavity by structure such as a post extending through the cavity in a generally mesial-distal direction, or alternatively may be held captive in the cavity by wall sections of the cavity that engage projections along outer occlusal and gingival edges of the clip. In this alternative, the clip also has a third section with an convex outer edge facing away from the archwire-receiving region of the clip, and the outer edge is in contact with a wall portion that is also preferably convex. The wall portion may be part of the base or alternatively may be part of a body that is connected to the base.

A number of other constructions are also possible. For example, the body and/or the base may be made of a material other than metallic material, such as a ceramic material (including, for example, translucent or transparent aluminum oxide) or a plastic material (such as fiber-reinforced polycarbonate). In addition, an archwire slot liner may be provided. The clips may also be constructed with third sections that extend at an angle other than 90 degrees relative to the direction of extension of the first and second sections, for use with appliances having torque in the base as described, for example, in applicant's pending continuation-in-part U.S. patent application entitled "Self-ligating Orthodontic Appliance with Clip", Ser. No. 11/317,346, filed Dec. 23, 2005.

All of the patents and patent applications mentioned above are hereby expressly incorporated by reference herein. The embodiments described in detail above and shown in the drawings are intended to exemplify the invention, and should not be deemed to limit the scope of the claims that follow.

The invention claimed is:

1. An orthodontic appliance comprising:
   a base;
   a body extending outwardly from the base;
   an archwire slot extending across the appliance in a generally mesial-distal direction;
   a post extending outwardly from the body; and
   a latch for releasably retaining an archwire in the archwire slot, wherein the latch comprises a clip with a first section, a second section opposed to the first section and a third section interconnecting the first section and the second section, wherein the clip also includes a region between the first section and the second section for receiving an archwire when an archwire is placed in the archwire slot, wherein the third section has an outer edge facing away from the archwire-receiving region, wherein the base includes a wall portion in contact with the outer edge, wherein the outer edge includes a portion near the middle of the third section that is in contact with the wall portion, and wherein at least this portion of the outer edge has a convex shape.

2. An orthodontic appliance according to claim 1 wherein the wall portion of the base also has a convex shape.

3. An orthodontic appliance according to claim 1 wherein the latch also includes a second clip.

4. An orthodontic appliance according to claim 3 wherein the second clip of the latch includes an outer edge having a convex shape and in contact with the base.

5. An orthodontic appliance according to claim 1 wherein the base and the body are integrally formed as a unitary component.

6. An orthodontic appliance according to claim 1 wherein the base, the body and the post are integrally formed as a single, unitary component.

7. An orthodontic appliance according to claim 1 wherein the clip has an overall, generally "C"-shaped configuration.

8. An orthodontic appliance according to claim 1 wherein the post includes a head and a neck interconnecting the head and the body.

9. An orthodontic appliance according to claim 1 wherein the base and the body are integrally formed as a unitary component and wherein the base includes one or more from the following group: grooves, projections, particles, recesses, undercuts and a chemical bond enhancement material.

10. An orthodontic appliance according to claim 9 wherein the base and the body are made of a metallic material.

11. An orthodontic appliance according to claim 1 wherein the outer edge has a smoothly curved convex shape along substantially its entire extent.

12. An orthodontic appliance comprising:
a base;
a body extending outwardly from the base;
an archwire slot extending across the appliance in a generally mesial-distal direction;
a latch for releasably retaining an archwire in the archwire slot, wherein the latch comprises a clip with a first section, a second section opposed to the first section and a third section interconnecting the first section and the second section, wherein the clip also includes a region between the first section and the second section for receiving an archwire when an archwire is placed in the archwire slot, wherein the third section has an outer edge facing away from the archwire-receiving region; and
structure for coupling the clip to the body, wherein the appliance includes a wall portion in contact with the outer edge, wherein the outer edge includes a portion near the middle of the third section that is in contact with the wall portion, and wherein at least this portion of the outer edge has a convex shape.

13. An orthodontic appliance according to claim 12 wherein the structure comprises a post.

14. An orthodontic appliance according to claim 12 wherein the wall portion comprises part of the base.

15. An orthodontic appliance according to claim 14 wherein the wall portion also has a convex shape.

16. An orthodontic appliance according to claim 12 wherein the latch also includes a second clip.

17. An orthodontic appliance according to claim 12 wherein the second clip of the latch includes an outer edge having a convex shape and in contact with the base.

18. An orthodontic appliance according to claim 12 wherein the base and the body are integrally formed as a unitary component.

19. An orthodontic appliance according to claim 12 wherein the clip has an overall, generally "C"-shaped configuration.

20. An orthodontic appliance according to claim 12 wherein the base and the body are integrally formed as a unitary component and wherein the base includes one or more from the following group: grooves, projections, particles, recesses, undercuts and a chemical bond enhancement material.

21. An orthodontic appliance according to claim 12 wherein the outer edge has a smoothly curved convex shape along substantially its entire extent.

22. An orthodontic appliance comprising:
a base;
a body extending outwardly from the base;
an archwire slot extending across the appliance in a generally mesial-distal direction;
a post extending outwardly from the body;
a latch for releasably retaining an archwire in the archwire slot, wherein the latch comprises a clip with a first section, a second section opposed to the first section and a third section interconnecting the first section and the second section, wherein the clip also includes a region between the first section and the second section for receiving an archwire when an archwire is placed in the archwire slot, wherein the third section has an outer edge facing away from the archwire-receiving region, wherein the base includes a wall portion in contact with the outer edge, wherein the outer edge in contact with the wall portion has a convex shape, wherein the third section includes opposite ends, and wherein the ends do not contact the base when an archwire is received in the archwire slot.

23. An orthodontic appliance comprising:
a base;
a body extending outwardly from the base;
an archwire slot extending across the appliance in a generally mesial-distal direction;
a latch for releasably retaining an archwire in the archwire slot, wherein the latch comprises a clip with a first section, a second section opposed to the first section and a third section interconnecting the first section and the second section, wherein the clip also includes a region between the first section and the second section for receiving an archwire when an archwire is placed in the archwire slot, wherein the third section has an outer edge facing away from the archwire-receiving region;
structure for coupling the clip to the body, wherein the appliance includes a wall portion in contact with the outer edge, wherein the outer edge in contact with the wall portion has a convex shape, wherein the third section includes opposite ends, and wherein the ends do not contact the base when an archwire is received in the archwire slot.

* * * * *